United States Patent [19]
Ashman

[11] Patent Number: 5,242,445
[45] Date of Patent: Sep. 7, 1993

[54] SPLIT EYEBOLT FOR SPINAL ROD

[75] Inventor: Richard B. Ashman, Dallas, Tex.

[73] Assignee: Danek Medical, Inc., Memphis, Tenn.

[21] Appl. No.: 802,609

[22] Filed: Dec. 5, 1991

[51] Int. Cl.⁵ .............................................. A61F 5/02
[52] U.S. Cl. ...................................... 606/61; 606/53; 606/73; 411/385
[58] Field of Search ..................... 606/53, 60, 61, 72, 606/73, 74; 24/276, 278; 411/385

[56] References Cited

U.S. PATENT DOCUMENTS

| | | | |
|---|---|---|---|
| 4,032,155 | 6/1977 | Thomas | 434/260 X |
| 4,641,636 | 2/1987 | Cotrel . | |
| 4,648,388 | 3/1987 | Steffee . | |
| 4,813,109 | 3/1989 | McCully et al. . | |
| 4,815,453 | 3/1989 | Cotrel . | |
| 5,122,131 | 6/1992 | Tsou | 606/61 |

OTHER PUBLICATIONS

*Danek Surgical Technique Manual TSRH ™ Spinal Implant System*, by Danek Medical, Inc. Feb. 1, 1990.
*Universal Instrumentation (CD) for Spinal Surgery*, by Drs. Cotrel and Dubousset, published by Stuart of Greensburg, Pa. 15601 (19 pages).
*DANEK Luque II Spinal System*, published by Danek Medical, Inc., Feb. 1, 1990.

Primary Examiner—Richard J. Apley
Assistant Examiner—Linda C. M. Dvorak

[57] ABSTRACT

A one piece item of stainless steel or other material suitable for permanent placement in the human body, forms the eye and shaft of an eyebolt by a combination of two shell-like portions, each having threaded bosses at distal ends thereof. The distal ends are placed around a spinal rod simultaneously with insertion of one of the shell-like portions through the yoke of a spinal column connecting hook device. Then the bosses are brought toward each other and the two bosses combine to form a bolt on which a nut is received and advanced along the threads. As this is done, it forms the eye of the eyebolt and it is brought into cooperation with the hook device to clamp tightly on a spinal rod with which the eyebolt is used. The two threaded bosses have interfitting, and thus mating, rib and groove to establish and maintain alignment of the threads of the two bosses to facilitate reception of the nut on the bosses. Thus, the connecting hook device can be installed and clamped to a spinal rod between other devices already installed on the spinal rod, without disturbing the other devices. Upon removal of the nut from the bosses, the eyebolt can be completely removed from the spinal rod without disturbing any other device attached to the spinal rod.

10 Claims, 4 Drawing Sheets

SPLIT EYEBOLT FOR SPINAL ROD

BACKGROUND OF THE INVENTION

1. Field of the Invention

This invention relates generally to implanted spinal fixation devices, and more particularly to a split eyebolt used on a spinal rod to secure a hook or other attachment device at any of various desired possible locations on the spinal rod.

2. Description of the Prior Art

In connection with certain corrective work for human spinal columns, spinal rods are disposed on both sides of the spinal column. Various types of attaching devices are placed along the length of the spinal rods and connected to the vertebrae in various ways. An example of such a device is shown in U.S. Pat. No. 4,648,388, issued on Mar. 10, 1987 to Steffee. This patent discloses "force transmitting members" 52 which are screwed into vertebrae and to which clamps are mounted. A spinal rod is placed in and secured to the clamps by tightening a nut on the end of the member 52 opposite that which is screwed into the vertebrae, thereby clamping the vertebrae to the spinal rod. Another arrangement, and which uses several types of hooks, rather than screws, for attachment to vertebrae, is shown in U.S. Pat. No. 4,641,636 issued on Feb. 10, 1987 to Cotrel. Another arrangement also using various types of hooks, but with an eyebolt on the rod to secure the hooks, is the "three-point shear" system of Danek Medical, Inc. Sometimes, during the course of the spinal implant operation, it can become evident that it is necessary or, at least, desirable to locate a fixation device someplace other than where previously thought necessary. In some instances it may be desirable to add a device or delete a device. With the type of arrangements shown in the aforementioned patents, that can be very inconvenient. With the Danek three-point shear system, although hooks can be readily added, prior to the present invention it was not so convenient to add eyebolts, because it was necessary to install them from one or the other end of the rod. The present invention was made in recognition of a need to provide some means to attach hooks or other anchoring devices to spinal rods and which can be installed between existing devices already attached to the spinal rods, and which also can be moved readily along the spinal rod during an implant procedure to place it in precisely the location desired without detaching the other devices.

SUMMARY OF THE INVENTION

Described briefly, according to a typical embodiment of the present invention, the eyebolt is a combination of two shell-like portions of a malleable metal suitable for permanent placement in the human body. The two portions have threaded bosses at distal ends thereof. When the distal ends are brought toward each other, the two bosses combine to form a bolt on which a nut is received and advanced along the threads. As this occurs, a central aperture through the eyebolt is brought into cooperation with an anchoring member to clamp tightly on a spinal rod with which the eyebolt is used. The two threaded bosses have interfitting, and thus mating, rib and groove to establish and maintain alignment of the threads of the two bosses to facilitate reception of the nut on the bosses. Upon removal of the nut from the bosses, the eyebolt can be completely removed from the spinal rod without disturbing any other device attached to the spinal rod.

DESCRIPTION OF THE PREFERRED EMBODIMENT

Figure 1:
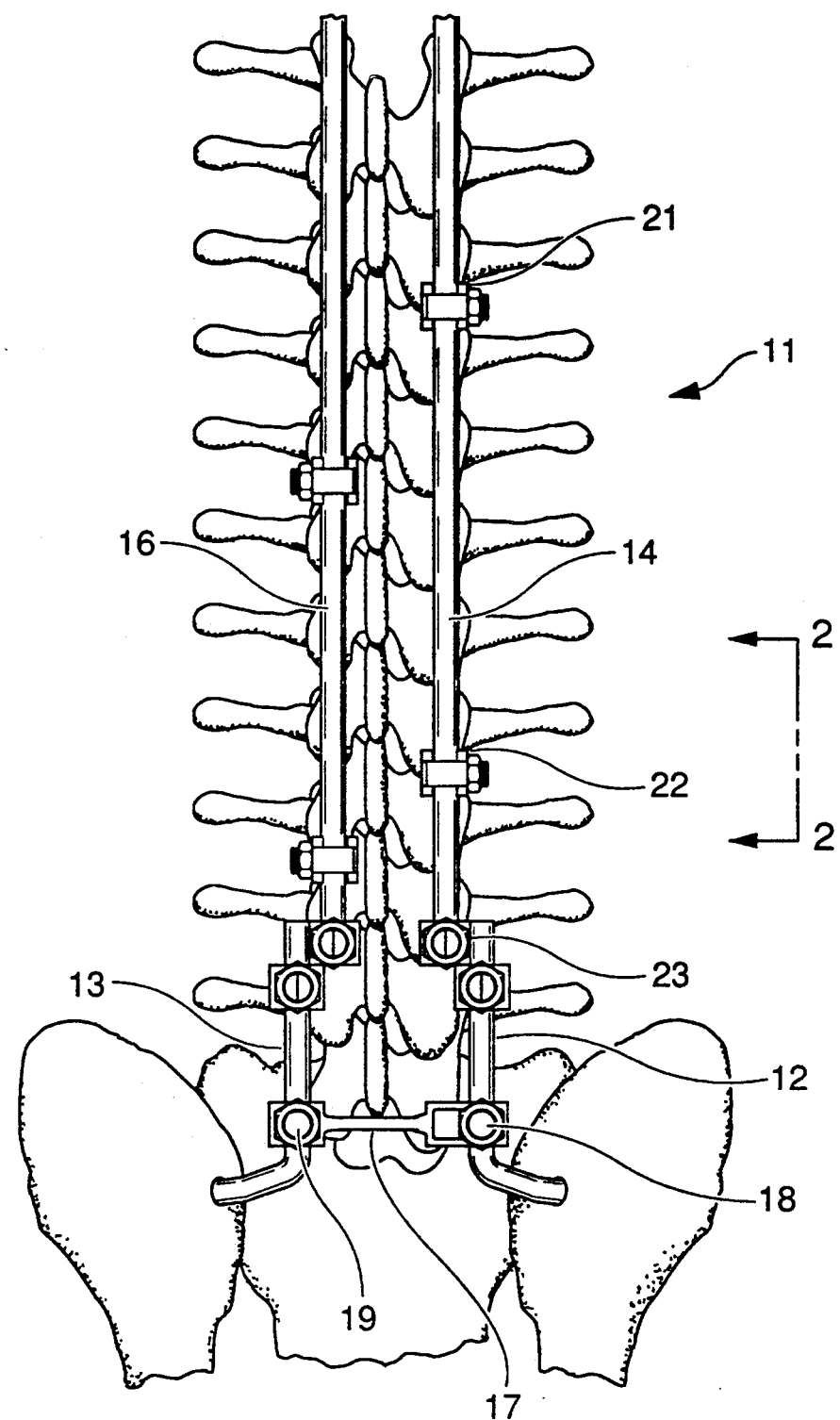
FIG. 1 is a fragmentary posterior view of a spinal column with corrective implant system incorporating the split eyebolt of the present invention.
Figure 2:
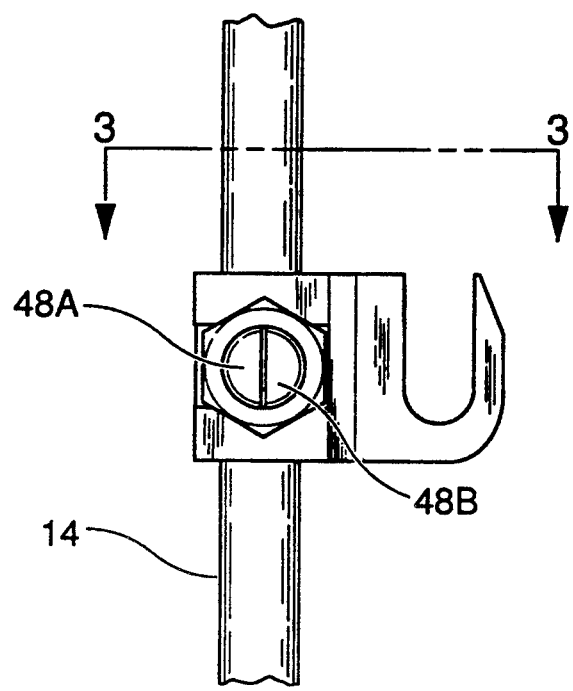
FIG. 2 is an enlarged fragmentary side elevational view taken at line 2—2 in FIG. 1 and viewed in the direction of the arrows and showing a hook affixed to a spinal rod with the split eyebolt according to a typical embodiment of the present invention.
Figure 3:
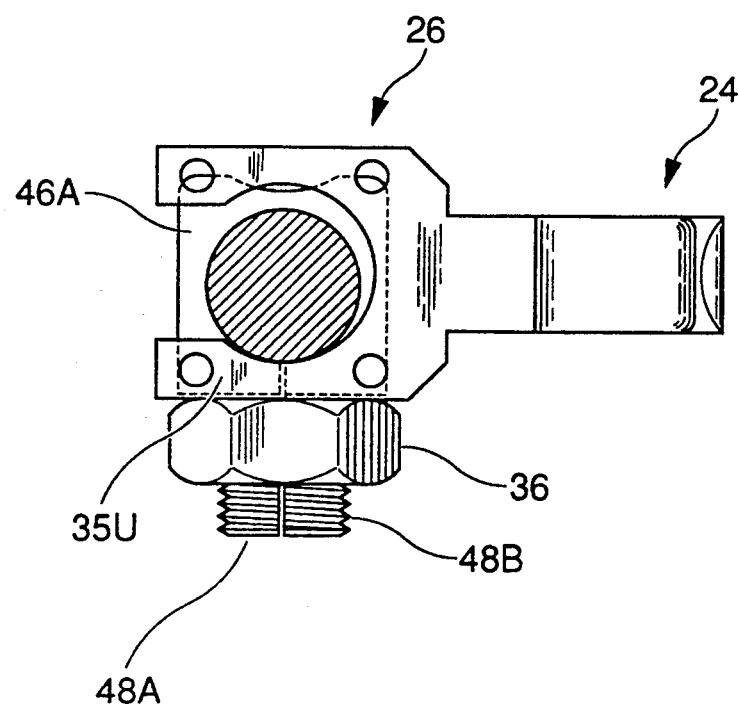
FIG. 3 is a section taken at line 3—3 in FIG. 2 and viewed in the direction of the arrows.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Figure 4:
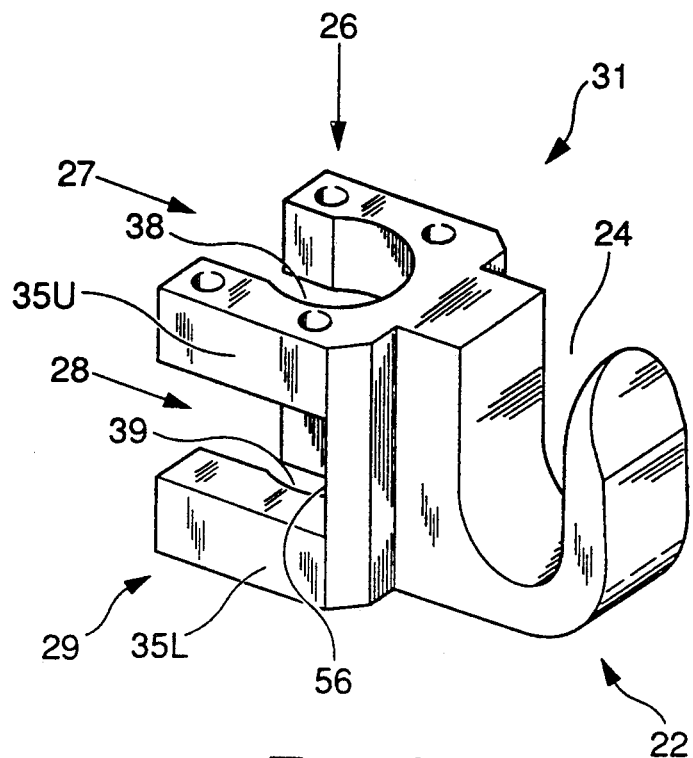
FIG. 4 is an enlarged pictorial view of the hook employed.

Referring now to the drawings in detail, FIG. 1 shows part of the pelvis and spinal column 11. There are four rods shown, two of them, rods 12 and 13 having their lower ends in the sacrum and two of them, 14 and 16 extending upward along the spinal column. An assortment of hooks is employed at spaced locations along rods 14 and 16 for connection of the rods to the vertebrae. In addition, hooks and spacers are connected to the rods 12 and 13. All of the hooks and spacers are clamped to the rods by eyebolts. For example, the spacer link 17 establishing the space between the rods 12 and 13 at the link location is affixed to the rods 12 and 13 by eyebolts 18 and 19, respectively. The rod 14 is connected to the illustrated portion of the spinal column by hooks 21, 22, and 23. The hooks may be constructed in a variety of shapes such as shown on page 6 in FIGS. 6 and 7 of the Danek Surgical Technique Manual for the TSRH TM Spinal Implant System, published by Danek Medical, Inc. of Memphis, Tenn., on Feb. 1, 1990. They have in common, a "three-point shear" clamp feature when combined with the eyebolt as described in that manual. One such hook is shown in FIG. 4 herein, wherein the hook 22 has a hooked "shoe" portion 24 with a base "hook top" portion which has four arms and may be referred to as a two-way double yoke unit. For example, as viewed from above in the direction of arrow 26 in FIG. 4, the two upper arms form an upper C-shaped yoke 27 and the two lower arms form a lower C-shaped yoke 28, both opening to the left. The internal wall of these yokes is semicircular about a common axis. These yokes are adapted to receive the spinal rod 14 pushed to the right into the yoke entrance. The arms also form two yokes 29 and 31 which also open to the left but are aligned in a direction perpendicular to the axis of the yokes 27 and 28.

Figure 5:
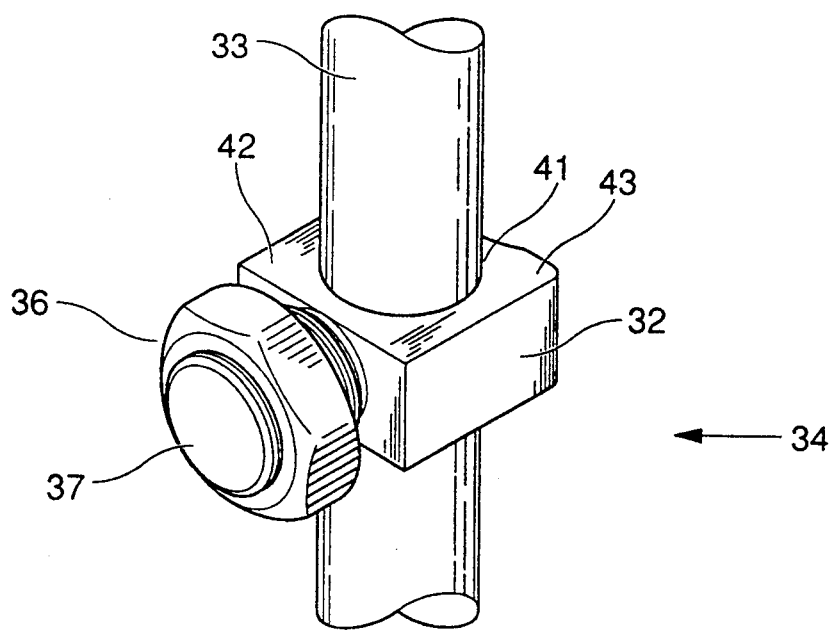
FIG. 5 is a pictorial view of a fragment of a spinal rod with a conventional eyebolt on it.

An eyebolt 32 of the previous TSRH Spinal Implant System, received on a spinal rod 33, can receive the hook top of FIG. 4 if the hook is advanced onto the rod in the direction of arrow 34 in FIG. 5. In so doing, the rod is received in the yokes 27 and 28, and the eyebolt base block 32 is received in the yokes 29 and 31. Then the nut 36 is tightened on the threaded stem 37 of the eyebolt and engages the faces of the upper and lower arms 35U and 35L of the hook top and pulls the eyebolt base 32 into yoke 29 between arms 35U and 35L and simultaneously pulls the spinal rod 33 into engagement with the semi-circular wall 38 on the inside of the upper arm 35U and the semi-circular wall 39 on the inside of the lower arm 35L and thereby clamps the spinal rod against that wall of the yoke 27, 28 of the hook top. The nut is tightened to 150 in-lbs. torque whereby the spinal rod is tightly gripped against walls 38 and 39 of yokes 27 and 28, respectively, and against the far wall 41 of the aperture through the eyebolt base 32. Thus is the origin of the term "three-point shear" clamp. As this clamping is accomplished, the forward end portion 42 of the eyebolt base is received in the yoke 29 between the upper and lower arms 35U and 35L of the hook forming that yoke, while the far end 43 of the eyebolt base may be received for a short distance in the yoke 31. It can be recognized from this description, that the hook and eyebolt are universal in the sense that the hook could be installed from the left in the direction opposite arrow 34 in FIG. 5, in which case the nut 36 would be engaging in the face of the other two arms of the hook top.

It can be recognized from the foregoing description that, with the prior art eyebolt on the rod as shown in FIG. 5, it is not possible to add or remove eyebolts except from the upper or lower end of the spinal rod. Therefore, if it is desired to add or remove a hook, it is can be inconvenient to do so.

According to the present invention, the same spinal rod as shown in FIGS. 1 or 5 can be used, and the same hook 22 can be used. However, the split eyebolt of the present invention is provided as shown in FIG. 6.

Figure 6:
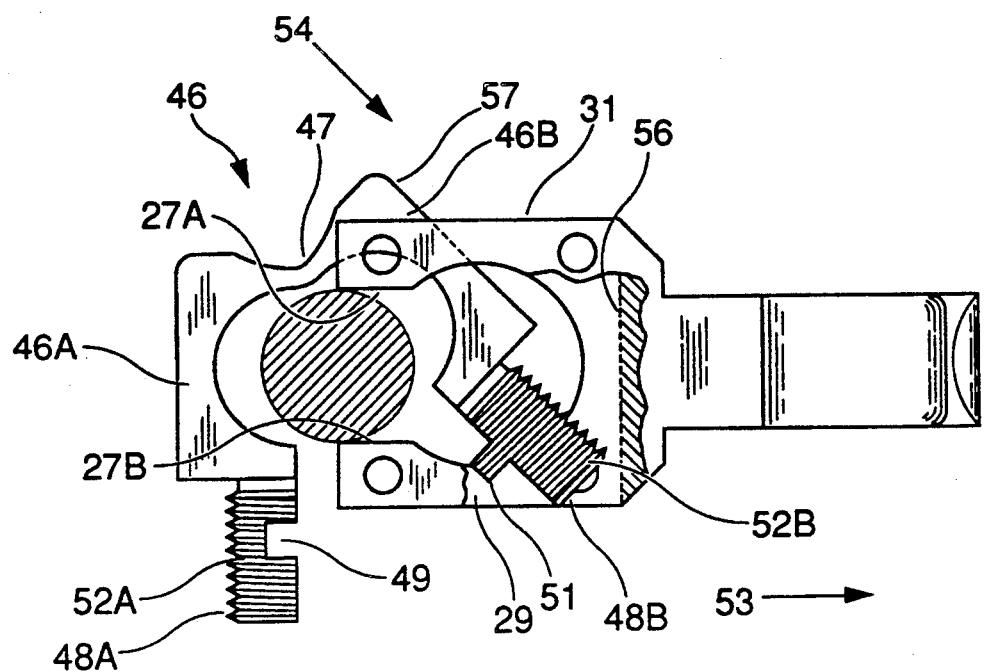
FIG. 6 is a view taken in the same direction as FIG. 3 and showing the eyebolt being installed through the yoke of the hook and around the spinal rod.
Figure 7:
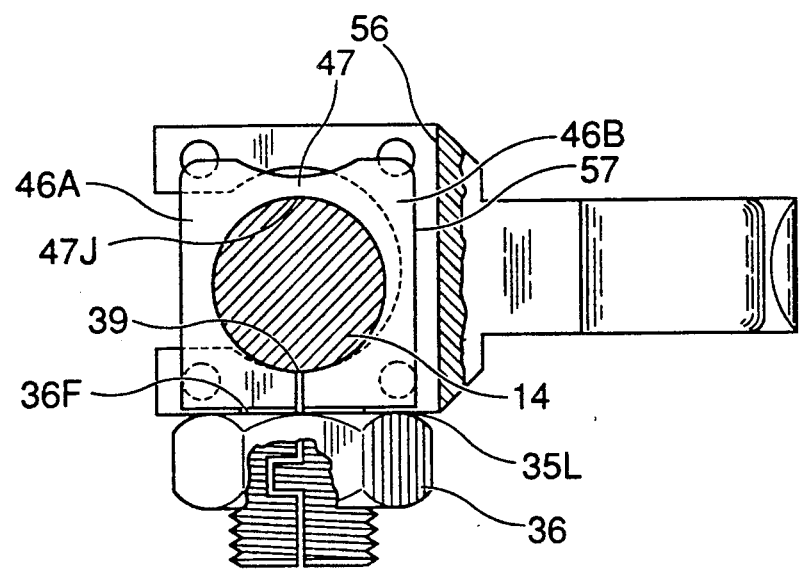
FIG. 7 is a view in the same direction as FIGS. 3 and 6 and showing the eyebolt installed and clamping the hook and rod together.

Referring now to FIG. 6, the split eyebolt according to the present invention would be provided with an initial configuration as shown in FIG. 6 where the base 46 comprises two generally C-shaped shells 46A and 46B of the same thickness as the standard eyebolt base 32 in FIG. 5, but joined at a narrow section 47. Each shell has a threaded boss 48A on shell 46A and 48B on shell 46B. When these two bosses are brought together as shown in FIG. 7, they form a threaded shaft to receive the nut 36, which may be operated just as previously described nut 36 on the standard eyebolt. Each of the bosses 48A and 48B has an interlock feature, a groove 49 being provided in boss 48A and a rib or lug 51 being provided in boss 48B. These assist in aligning and maintaining alignment of the threads 52A and 52B on bosses 48A and 48B, respectively, so as to readily receive the nut 36.

To install an eyebolt of the present invention on a spinal rod after a new hook location is established, and after eyebolts and hooks have been already located along the rod at points spaced to either side of the desired additional installation, it is only necessary to move the hook relative to the rod in the direction of arrow 53 in FIG. 6 so that the rod is out of the way of insertion of boss 48B and shell 46B through yokes 31 and 29. The gap between the ends 27A and 27B at the entrance to the yoke 27 and corresponding gap at the entrance of yoke 28, are slightly greater than the diameter of the rod 14, and thus enable moving the rod in and out of the yokes. Then the threaded boss 48B of the eyebolt is inserted in the direction of arrow 54 through the yokes 31 and 29, respectively. Then the ends of the eyebolt can be brought together with the rib 51 being received in the groove 49 as the eyebolt closes around the spinal rod. Simultaneously, the spinal rod can be moved back into the yoke 27. Then the nut 36 is installed on the eyebolt thread bosses as shown in FIG. 7 and advanced on the threads so that the face 36F of the nut abuttingly engages the outside faces of upper arm 35U (broken away in FIG. 7) and lower arm 35L, of the hook top. As it does so and is further tightened, it pulls the spinal rod tightly against the semi-circular inner face 39 of the lower arm 35L of the hook base and against the semi-circular inner face 38 (not shown in FIG. 7) of upper arm 35U as the semi-circular surface 47J at the transition 47 of shells 46A and 46B tightly engages the opposite surface of the spinal rod. Thus, the three-point shear clamping system is achieved, but with an eyebolt according to the present invention which can be readily installed anyplace along the length of the spinal rod, even though there are other eyebolts or other attaching devices already installed on the spinal rod outboard of the desired location for the additional eyebolt.

After installation, the configuration of the eyebolt of the present invention is readily maintained in proper alignment with the hook top by the wall 56 of the hook top facing the wall 57 of the split eyebolt. Thus, even before tightening the nut on the split eyebolt, the relationship of the eyebolt to the hook is reasonably well established so that, when it is desired to apply some torque to the spinal column relative to the spinal rod, or simply provide the correct attitude of the hook with relation to the spinal rod, it can be done with the hook and eyebolt readily rotated on the spinal rod, as needed. Thus, the various attitudes of the hooks and eyebolts shown in FIG. 1 can be readily achieved.

The material to be used with the split eyebolt of the present invention is stainless steel. However other materials could be used. It is not intended that it be opened and closed repeatedly, lest there be undue stress imparted at the location 47.

It should be understood that the eyebolt of the present invention can be used along with the standard eyebolts as previously described, in various locations along the spinal rod. However, all of the eyebolts can be of the construction of the present invention, and it may be preferable that all be of this type and used at various locations on the spinal rods as shown in FIG. 1. The reason for this is the fact that it makes possible the addition, removal and relocation of hooks and their fastening eyebolts, relatively convenient during the implant procedure. Thus, while it may be desirable to have all locations of hooks and other anchoring devices predetermined before surgery begins, the present invention makes it possible to change the types of anchors and their locations during the surgical procedure and thereby assist with any unanticipated developments and, facilitates improved technique.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A split eyebolt for connecting spinal column attachment devices to a spinal rod and comprising:
   a ring defining an aperture sized for receiving a spinal rod therethrough and having a split therethrough defining a central axis;
   a pair of bosses projecting outwardly from said ring, one at each side of the split, each of the bosses having external threads thereon which, when the bosses are proximate each other, provide a threaded shaft for reception of nut thereon;
   wherein the split in the ring is in a plane containing the central axis and extends into the bosses, and the bosses have interfitting means thereon projecting across the plane;
   wherein the interfitting means are a rib in one boss and a groove in the other boss receiving the rib of the one boss, and wherein the rib has external threads.

2. A method of making a further connection of a spinal rod in a system for correcting spinal deformities to the spinal column, wherein the spinal rod is already connected to the spinal column by anchoring devices attached to the spinal column and to the spinal rod at spaced points along the rod, the method comprising the steps of:
   placing a hook shoe around a spinal bone;
   placing an eyebolt around the spinal rod at a location on the rod between anchoring devices without disconnecting the anchoring devices from the spinal rod; and
   securing the eyebolt to the hook shoe by threading a nut onto the eyebolt.

3. The method of claim 2 and wherein the step of placing the eyebolt includes:
   placing the rod between two bosses of the eyebolt, the bosses having threaded external surfaces; and
   then bringing the bosses together to form a continuous threaded outer surface.

4. The method of claim 3 and further comprising the step of:
   inserting an alignment rib of one arm into an alignment groove in the other arm while bringing the arms together to facilitate mounting the nut on the continuous threaded outer surface.

5. The method of claim 3 and wherein the securing step includes:
   moving the eye of the eyebolt in a hook top fixed to the hook shoe; and
   turning a nut on the continuous external threaded surface and engaging the hook top with the nut while using the nut to pull the eyebolt and thereby pull the spinal rod in a direction transverse to its axis and into tight abutting engagement with the hook top.

6. The method of claim 5 and wherein the securing step further includes the step of:
   moving the eyebolt eye into a yoke in the hook top.

7. The method of claim 5 and wherein the securing step further includes the step of:
   blocking rotation of the eyebolt eye in the yoke during the use of the unit to pull the spinal rod into tight abutting engagement.

8. A system for correcting spinal deformities comprising:
   a spinal rod;
   a number of anchoring devices for attachment to the spinal column and to the spinal rod at spaced points along the rod;
   a hook having a hook shoe for engaging a portion of the spinal column and having a hook for engaging the spinal rod;
   a threaded eyebolt to be received in the hook top and having threads thereon, the eyebolt being split along its threads; and
   a nut for engaging the threads of the eyebolt for clamping the hook top between the nut and the spinal rod.

9. The system of claim 8 and wherein:
   the eyebolt has an eye portion with an aperture having an axis, and the eyebolt has threaded shaft portion extending outward from the eye portion and defining a shaft axis intersecting the axis of the eye,
   the shaft portion being split longitudinally from the aperture outward to the outer end of the shaft portion.

10. The system of claim 9, wherein:
    the threaded shaft portion split is along a plane containing the shaft axis and defines an interengaging rib and groove combination extending generally perpendicular to the shaft axis intermediate along the length of the shaft portion.

* * * * *